United States Patent [19]
Nakashima et al.

[11] Patent Number: 6,139,838
[45] Date of Patent: *Oct. 31, 2000

[54] TISSUE PLASMINOGEN ACTIVATOR MEDICINAL COMPOSITION

[75] Inventors: Kazuyuki Nakashima; Yoshitaka Tajima; Shinichi Furukawa; Hiroshi Mizokami, all of Kumamoto, Japan

[73] Assignee: Juridical Foundation The Chemo-Sero-Therapeutic Research Institute, Kumamoto, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/923,999

[22] Filed: Sep. 5, 1997

[30] Foreign Application Priority Data

| Sep. 6, 1996 | [JP] | Japan | ................................. | 8-257752 |
| Apr. 30, 1997 | [JP] | Japan | ................................. | 9-128083 |
| Apr. 30, 1997 | [JP] | Japan | ................................. | 9-128084 |

[51] Int. Cl.⁷ .......................... A61K 38/48; A61K 31/70; C12N 9/48; A01N 43/04
[52] U.S. Cl. .................................. 424/94.64; 424/94.63; 514/42; 514/43; 435/212
[58] Field of Search ............................ 424/94.63, 94.64; 435/212, 226, 359; 514/42, 43

[56] References Cited

U.S. PATENT DOCUMENTS

| 4,898,826 | 2/1990 | Duffy et al. | ............................. | 135/226 |
| 4,929,444 | 5/1990 | Johnston et al. | ...................... | 424/94.64 |
| 4,935,237 | 6/1990 | Higgins et al. | ....................... | 424/94.64 |
| 4,968,617 | 11/1990 | Johnston et al. | ...................... | 424/94.63 |
| 5,037,646 | 8/1991 | Higgins et al. | ....................... | 424/94.64 |
| 5,112,609 | 5/1992 | Johnston et al. | ...................... | 424/94.64 |
| 5,589,361 | 12/1996 | Hotchkiss et al. | ...................... | 435/69.1 |

FOREIGN PATENT DOCUMENTS

| 0 112 940 | 7/1984 | European Pat. Off. . |
| 0 196 920 | 10/1986 | European Pat. Off. . |
| 0 199 574 | 10/1986 | European Pat. Off. . |
| 0 217 379 | 4/1987 | European Pat. Off. . |
| 0 303 251 | 2/1989 | European Pat. Off. . |
| 0 493 037 | 7/1992 | European Pat. Off. . |
| 54-070419 | 6/1979 | Japan . |
| 61-243024 | 10/1986 | Japan . |
| 62-24 | 1/1987 | Japan . |
| 63-501335 | 5/1988 | Japan . |
| 63-133988 | 6/1988 | Japan . |
| 63-38327 | 7/1988 | Japan . |
| 1-221325 | 9/1989 | Japan . |
| 2-504102 | 11/1990 | Japan . |
| 3-500843 | 2/1991 | Japan . |
| 3-29390 | 4/1991 | Japan . |
| 3-69332 | 10/1991 | Japan . |
| 5-27607 | 4/1993 | Japan . |
| 6-72105 | 9/1994 | Japan . |
| 6-99324 | 12/1994 | Japan . |
| 2518832 | 5/1996 | Japan . |
| WO 87/04722 | 8/1987 | WIPO . |
| WO 96/07429 | 3/1996 | WIPO . |

OTHER PUBLICATIONS

Harris, T.J.R. *Protein Engineering* 1(6):449–458 (1987).
Database WPI, Derwent Publications, AN 79–53236B, JP 54–070419, Jun. 6, 1979.
Database WPI, Derwent Publications, AN 93–278215, JP 5–194265, Aug. 3, 1993.
Yoshimasa Saito, et al., Biotechnology Progress, vol. 10, No. 5, pp. 472–479, "Production and Characterization of a Novel Tissue–Type Plasminogen Activator Derivative in *Escherichia Coli*", 1994.
Pharmacopeial Previews, pp. 1222–1230, "Monographs", Nov.–Dec. 1990.
J. Truelove, et al., International Journal of Pharmaceutics, vol. 19, pp. 17–25, "Solubility Enhancement of Some Developmental Anti–Cancer Nucleoside Analogs by Complexation with Nicotinamide", 1984.
Richard A. Kenley, et al., Journal of Pharmaceutical Sciences, vol. 75, No. 7, pp. 648–653, "Water Soluble Complexes of the Antiviral Drugs, 9–[(1, 3–Dihydroxy–2–Proproxy)Methyl]Guanine and Acyclovir: The Role of Hydrophobicity in Complex Formation", Jul. 1986.
Alaa Abdul Rasool, et al., Journal of Pharmaceutical Sciences, vol. 80, No. 4, pp. 387–393, "Solubility Enhancement of Some Water–Soluble Drugs in the Presence of Nicotinamide and Related Compounds", Apr. 1991.

*Primary Examiner*—Karen Cochrane Carlson
*Assistant Examiner*—Holly Schnizer
*Attorney, Agent, or Firm*—Oblon, Spivak, McClelland, Maier & Neustadt, P.C.

[57] ABSTRACT

The present invention provides a t-PA medicinal preparation obtained by remarkably improving the solubility and stability of t-PA or modified t-PA. Nicotinamide or a derivative thereof is incorporated into t-PA or modified t-PA-containing solvent system. If necessary, a citrate buffer solution is also used. The t-PA-containing medicinal composition is in the form of, for example, a freeze-dried preparation.

17 Claims, 1 Drawing Sheet

TISSUE PLASMINOGEN ACTIVATOR MEDICINAL COMPOSITION

BACKGROUND OF THE INVENTION

The present invention relates to a medicinal composition containing a tissue plasminogen activator (hereinafter referred to also as "t-PA"). In particular, the present invention relates to a t-PA or a modified t-PA-containing medicinal composition, characterized by containing t-PA or modified tissue plasminogen activator (hereinafter referred to also as "modified t-PA") and nicotinamide or a derivative thereof.

t-PA activates plasminogen to form plasmin which dissolves fibrin which is the main component of the protein substrate of the thrombus. t-PA preparations were developed as a thrombolytic agent having a very high selectivity toward the thrombus in the thrombolytic treatment for thrombosis which causes myocardial infarction and cerebral infarction. Further, various modified t-PA's were also produced by genetic engineering for the purpose of obtaining higher affinity to fibrin and the half-life in blood than those of the natural t-PA. The modified t-PA's thus produced from procaryotes are of non-glycosyl type unlike the natural t-PA. t-PA's are proteins generally extremely difficultly soluble in water. In particular, the modified t-PA's are more difficultly soluble in water than natural t-PA to make very difficult the preparation thereof and the preparation of injections or the like to be dissolved in water at the time of the administration to a patient, while the modified t-PA's have various advantages such as increase in the affinity to fibrin and elongation of the half-life in blood.

The basic idea in the recent treatment of acute myocardial infarction is that, when the coronary arteries are blocked up, the blood circulation is to be recovered as immediately as possible to minimize the cardiac disorder. According to this idea, a drug of a high concentration which can be safely administered in a short time is preferred. Therefore, when the recirculation of the blood in the coronary arteries in an early stage and the prevention of the blocked portion from the enlargement are expected in using the modified t-PA having the various advantages, it is preferred to immediately administrate the preparation having a high t-PA concentration once. Under these circumstances, the development of a t-PA preparation having an improved water solubility, high concentration and stable protein structure is demanded, even though t-PA's, particularly glycosyl-free t-PA's, are difficultly soluble in water and have an unstable protein structure.

In addition, t-PA's including the modified t-PA's are generally unstable to heat. To develop such substances usable as medicines, a technique for stabilizing them is also indispensable.

As for the prior technique for solubilizing t-PA, a technique wherein t-PA is solubilized and stabilized by adding arginine hydrochloride or a salt thereof to t-PA under neutral to weakly alkaline condition is known [see Japanese Patent Publication for Opposition Purpose (hereinafter referred to as "J. P. KOKOKU") Nos. Hei 6-72105 and 6-99324]. However, the defect of this technique is that the stability of the protein structure of t-PA in a high concentration is reduced under the neutral to weakly alkaline condition. As for the solulbility, the dissolving properties of the glycosyl-free t-PA and modified, glycosyl-free t-PA are different from those of the natural t-PA, and the redissolution of the self-associated t-PA by this technique has been difficult.

Further, a process for solulbilizing t-PA by controlling the solution at pH 2 to 5 is known (see J. P. KOKOKU Nos. Sho 63-38327 and Hei 3-69332). However, for obtaining the intended preparation, this process still has some problems to be solved because freeze-dried t-PA or a t-PA solution is rapidly decomposed and deactivated.

On the other hand, the following processes for stabilizing t-PA have been known in the prior art: a process wherein albumin is added (J. P. KOKOKU No. Hei 3-29390), a process wherein a decomposition product of albumin is added [Japanese Patent Unexamined Published Application (hereinafter referred to as "J. P. KOKAI") No. Hei 1-221325) and a process wherein gelatin treated with an acid is added (J. P. KOKOKU No. Hei 5-27607). However, it has been confirmed that the effects of these processes are unsatisfactory when the concentration of t-PA is high and that the solubility of t-PA in a citric acid buffer solution is reduced particularly by the addition of albumin.

SUMMARY OF THE INVENTION

The object of the present invention is to provide a process for improving the solubility of a t-PA or modified t-PA composition having a low solulbility and stability and also to provide a t-PA medicinal preparation containing the t-PA or modified t-PA in the form of a solution having a concentration suitable for the clinical use and also having a pharmaceutically sufficient stability.

After intensive investigations made for the purpose of solving the above-described object, the inventors have found that surprisingly, the solubility of a preparation comprising t-PA or modifed t-PA is remarkably improved when nicotinamide or a derivative thereof is incorporated thereinto. The inventors have also found that the stability of t-PA in the composition containing nicotinamide is remarkably improved irrespective of the form (freeze-dried or liquid) thereof. On the basis of these findings, the inventors have completed the present invention, which provides a new process for improving the solubility of t-PA or modified t-PA and also a t-PA composition containing the t-PA or modified t-PA and nicotinamide or a derivative thereof.

DESCRIPTION OF THE PREFERRED EMBODIMENT

Figure 1:
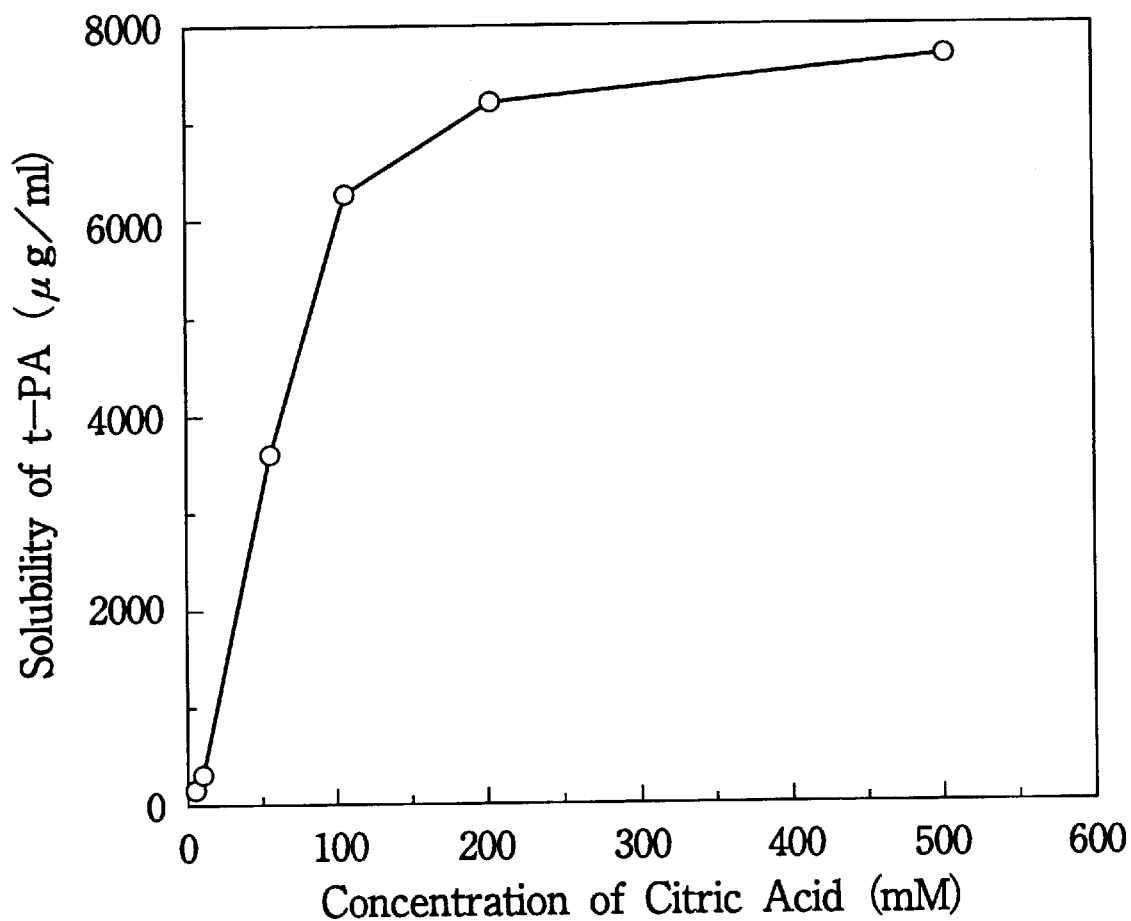
FIG. 1 shows the influence of citric acid concentration on the solubility of t-PA.

The detailed description will be made on the present invention below.

t-PA used in the present invention includes not only natural t-PA derived from human beings but also a glycosyl derivative of t-PA or glycosyl-free t-PA obtained by a genetic engineering technique.

The modified t-PA usable in the present invention is obtained from t-PA by a point mutation method or the like or by improving the biological activity of t-PA. Any modified t-PA is usable so far as the solubility-improving effect and stabilization effect of the present invention can be attained. The preferred, modified t-PA's are disclosed in, for example, J. P. KOKAI Nos. Sho 61-243024, 62-24 and 63-133988 and Japanese Patent Unexamined Published Application (hereinafter referred to as "JP Kohyo") Nos. Sho 63-501335, Hei 2-504102 and Hei 3-500843.

The modified t-PA's usable in the present invention include those listed below:

(1) modified t-PA obtained by replacing Val at the 245-position of the t-PA with Met, (2) modified t-PA obtained by replacing Cys at the 84-position of the t-PA with Ser, (3) modified t-PA obtained by partially deleting the F and G domains of t-PA and replacing Asn at the 117-position with Glu, (4) modified t-PA obtained by deleting the K1 domain of t-PA and replacing Arg at the 275-position with Glu, and (5) modified t-PA obtained by deleting the F, G and K1 domains of t-PA.

t-PA or modified t-PA is used in an amount of, for example, 0.005 to 1% by weight, preferably 0.01 to 0.5% by weight, and particularly 0.1 to 0.2% by weight, based on the medicinal composition of the present invention.

The safety of t-PA or modified t-PA has been confirmed from the clinical results obtained hitherto.

Nicotinamide used in the present invention is a factor of a water-soluble vitamin $B_2$ composite, and usually 10 to 20 mg/day or more of nicotinamide must be taken by adults. Nicotinamide is given in The Pharmacopoeia of Japan, and is clinically used for the prevention and treatment of a nicotic acid deficiency disease. As for the toxicity of nicotinamide, it was reported that the lethal dose for mice is 2 to 3 g/kg, and that a massive dose of nicotinamide can be given to human beings because no toxicity is recognized even when 500 mg/day of nicotinamide is administered everyday.

The safety of t-PA itself has been confirmed by the clinical results obtained hitherto. Thus, the t-PA preparation containing nicotinamide is considered to have an extremely high safety. Although known pharmacological effects of nicotinamide are substantially equal to those of nicotinic acid, nicotinamide does not accelerate the vascular permeability unlike nicotinic acid. Thus, as for the pharmacological effect of nicotinamide known hitherto, nicotinamide has substantially no influence on the blood system. Nicotinamide is considered to be an ideal medicinal additive free from the interaction between the pharmacological effect thereof and that of t-PA.

Nicotinamide used in the present invention may be a derivative thereof selected from among, for example, N-alkyl-substituted nicotinamides such as N-methylnicotinamide and N,N-diethylnicotinamide (the preferred alkyl substituents being, for example, linear or branched alkyl groups having 1 to 5 carbon atoms, desirably 1 to 3 carbon atoms), nicotinamide derivatives having a ring-substituting alkyl group (the preferred alkyl groups being, for example, linear or branched alkyl groups having 1 to 5 carbon atoms, desirably 1 to 3 carbon atoms) such as 1-methylnicotinamide, and isonicotinamide. Among them, nicotinamide given in The Pharmacopoeia of Japan is an optimum embodiment.

Nicotinamide or a derivative thereof is used in an amount of usually 0.1 to 50% (w/v %; the same shall apply hereinafter), preferably 0. 3 to 5% and practically preferably 1 to 3%, based on the medicinal composition of the present invention. By using nicotinamide or a derivative thereof in an amount in this range, the solubility of t-PA or modified t-PA can be improved.

The medicinal composition of the present invention may contain, if necessary, additives usually used for the preparation of medicines such as an isotonizer, e.g., sodium chloride or potassium chloride; a filler, e.g., mannitol or albumin; a stabilizer; and a nonionic surfactant, e.g., polysorbate 80 (trade name: Tween 80) in addition to t-PA or modified t-PA and nicotinamide or a derivative thereof.

The medicinal composition of the present invention may be used in the form of a solid composition, aqueous composition or two-pack preparation in which t-PA is packed separately from nicotinamide or its derivative and from which an injection is to be prepared at the time of use. The two-pack preparation comprises, for example, a combination of t-PA-containing freeze-dried vial and a soluton vial containing nicotinamide or a derivative thereof.

The medicinal composition of the present invention can be produced by various methods. For example, this medicinal composition can be produced by adding nicotinamide or a derivative thereof to t-PA or modified t-PA in a suitable medium. The medium is preferably selected from among various buffer solutions. The buffer solutions usable herein include those containing, for example, tris hydrochloride, phosphoric acid, carbonic acid, boric acid, citric acid, acetic acid, tartaric acid, succinic acid or an amino acid.

For the medicinal composition of the present invention, a citrate buffer solution containng citric acid is preferred because it synergistically improves the solubilizing effect of nicotinamide or its derivative.

When the citrate buffer solution is incorporated into the medicinal composition of the present invention, the citric acid content (the total amount of citric acid itself and citric acid in the form of the citrate) of the resultant composition is preferably 10 to 500 mM and particularly preferably 10 to 50 mM in practice.

pH of the medicinal composition of the present invention is usually 4 to 6.5, preferably 5 to 6. In particular, it has been found that at a pH in the range of 5 to 6, the stability of t-PA and modified t-PA is improved and the resistance thereof to the modification on the amino acid level by heating or aging is further improved.

The medicinal composition of the present invention can be produced by a process wherein a t-PA-containing fraction eluted by the chromatography is replaced with, for example, a citrate buffer solution containing nicotinamide or its derivative, or a process wherein the t-PA-containing fraction is dialyzed against water to form t-PA precipitate and then the precipitate is dissolved in, for example, a citrate buffer solution containing nicotinamide or its derivative. In such a process, it is possible to finally incorporate nicotinamide or its derivative and, if necessary, another preparation base such as citrate buffer solution into the product obtained as described above and then to control the t-PA concentration as desired or to freeze-dry the liquid under sterile conditions. Particularly, according to the present invention, the freeze-dried t-PA preparation containing t-PA or modified t-PA in a concentration suitable for the clinical use and having a pharmaceutically sufficient stability can be easily obtained.

The freeze-dried preparation is produced by freeze-drying the t-PA- or modified t-PA-containing solution, obtained as described above, by an ordinary method. For example, the solution is sterilized by filtration or the like and then a desired volume of the solution is fed into sterile glass vessels such as ampules or vials. The solution in the ampules or vials are frozen at a temperature of, for example, −50 to −10° C. The frozen solution is kept at a suitable temperature (for example, −50° C.) until the vacuum drying is started.

The frozen solution can be suitably dried in vacuo. For example, the frozen solution is dried under a partial vacuum or complete vacuum under 0.01 to 0.1 Torr for a period sufficient for substantially completely removing the frozen liquid. The vacuum drying temperature is usually such that the solution can be kept in substantially or completely frozen state. The initial temperature in the vacuum drying step is usually −30 to −40° C. As the water is gradually removed in the process, the temperature may be gradually elevated to room temperature. To remove the trace of water remaining in the final stage as far as possible, it is preferred to conduct the vacuum drying under substantial vacuum of about 0.01 Torr at room temperature or a temperature slightly above it after the completion of the treatment. The resultant t-PA freeze-dried product has a water content (moisture content) of preferably not higher than 2.5%. After the completion of the vacuum drying, the sterile glass vessel containing the freeze-dried t-PA is sealed while the reduced pressure is kept or after nitrogen gas is filled.

The freeze-dried medicinal preparation containing a high concentration of t-PA or modified t-PA can be advantageously obtained by the present invention. A t-PA-containing solution to be administered to a patient is prepared by the reconstitution from the freeze-dried t-PA medicinal preparation of the present invention with water at a neutral or acidic pH. When the aqueous solution from which the freeze-dried t-PA medicinal preparation is obtained is substantially isotonic, water used for the reconstitution is preferably substantially isotonic.

EXAMPLES

The present invention will be further illustrated with reference to the following Preparation Examples and Examples, which by no means limit the scope of the invention.

Preparation Example 1
(Preparation of Modified t-PA)

Purified, modified t-PA obtained by deleting the F, G and K1 domains of t-PA and replacing Arg at the 275-position with Glu was prepared by a method described in Biotechnology Progress, 10 (5); 472 to 479 (1994). The purified, modified t-PA was dialyzed against purified water and centrifuged. The obtained precipitate was stored at −80° C.

Preparation Example 2
(Preparation of Natural t-PA)

Natural t-PA ("GRTPA"; a product of Tanabe Seiyaku Co., Ltd.) comprising a complete molecule derived from recombinant CHO cells was prepared. The natural t-PA was dialyzed against purified water and centrifuged. The obtained precipitate was stored at −80° C. At the time of the use, it was adjusted to a concentration of about 8 mg/ml and used together with nicotinamide or its derivative of a predetermined concentration.

Test Example 1
(Solubility Test 1)

About 8 mg of the modified t-PA obtained in Preparation Example 1 was taken in a test tube, a buffer solution having a composition shown in Table 1 given below was added thereto. The obtained mixture was stirred and centrifuged to obtain a supernatant liquid. t-PA in the supernatant liquid activated plasminogen to form plasmin. t-PA activity was determined by hydrolysis activity of the resultant plasmin on synthetic substrate (S-2288) specific to plasmin, and then the solubility of t-PA was determined on the basis of standard t-PA sample of a known concentration. The results are given in Table 1.

TABLE 1

| Sample No. | Composition of buffer solution | Solubility (µg/ml) |
|---|---|---|
| 1 | 0.2M Arg/0.01% Tween 80/50 mM phosphate buffer (pH 7.2) | 151 |

TABLE 1-continued

| Sample No. | Composition of buffer solution | Solubility (µg/ml) |
|---|---|---|
| 2 | 100 mM citrate buffer (pH 5.6) | 186 |
| 3 | 5% Nicotinamide/0.01% Tween 80/100 mM citrate buffer (pH 5.6) | 7280 |
| 4 | 10% Nicotinamide/0.01% Tween 80/100 mM citrate buffer (pH 5.6) | 8417 |

It is apparent from Table 1 that the solubility of the nicotinamide-containing medicinal compositions is at least about 50 times as high as that of the arginine (Arg)-containing medicinal composition. It is thus apparent that nicotinamide in the medicinal composition of the present invention has a remarkable effect of increasing the solubility of modified t-PA.

When the solubility test 1 was repeated except that the concentration of citric acid in the citrate buffer was altered to 40 mM, the results similar to those described above were obtained.

Test Example 2
(Solubility Test 2)

The solubility test 1 was repeated except that nicotinamide concentration in the samples 3 and 4 was altered as shown in Table 2 given below to determine the solubility of t-PA. The results are shown in Table 2.

TABLE 2

| Nicotinamide conc. (%) | t-PA solubility (µg/ml) |
|---|---|
| 0 | 247 |
| 0.3 | 424 |
| 1 | 1065 |
| 2.5 | 3816 |
| 3 | 4392 |
| 4 | 6871 |
| 5 | >7370 |

It is apparent from the results shown in Table 2 that the solubility of the modified t-PA is increased as nicotinamide concentration in the medicinal composition of the present invention is increased. It is also apparent from the results that when at least 0.3% of nicotinamide is contained in the solution, a t-PA solubility completely satisfactory for the practical clinical use can be obtained.

Test Example 3
(Solubility Test)

The solubility of modified t-PA was determined in the same manner as that of Test Example 1 except that the kind of a buffer solution in the mixture containing 5% of nicotinamide, 1% of mannitol and 0.01% of Tween 80 was varied. The results are shown in Table 3.

TABLE 3

| Sample No. | Composition of buffer solution | Solubility (µg/ml) |
|---|---|---|
| 5 | 5% nicotinamide/0.01% Tween 80/1% mannitol/ 40 mM citrate buffer (pH 5.6) | >8407 |
| 6 | 5% nicotinamide/0.01% Tween 80/1% mannitol/ 200 mM acetate buffer (pH 5.7) | 5403 |
| 7 | 5% nicotinamide/0.01% Tween 80/1% mannitol/ 100 mM phosphate buffer (pH 6.0) | 2153 |

It is apparent from the results shown in Table 3 that when the citrate buffer solution is used, the solubility of t-PA is far more increased than that increased by using another buffer solution.

Test Example 4
(Solubility Test 4)

The solubility of t-PA was determined in the same manner as that of Test Example 1 except that the concentration of citric acid in the citrate buffer solution in the buffer solution (2.5% nicotinamide/1% mannitol/0.01% Tween 80/citrate buffer, pH 5.6) for dissolving t-PA was varied. The results are shown in Table 4 and FIG. 1.

TABLE 4

| Citric acid conc. (%) | t-PA solubility ($\mu$g/ml) |
|---|---|
| 5 | 157 |
| 10 | 305 |
| 50 | 3622 |
| 100 | 6265 |
| 200 | 7184 |
| 500 | 7677 |

It is apparent from the results of Test Example 4 that the t-PA solubility-increasing effect of nicotinamide is increased with the concentration of the citrate ion source (upper limit: 500 mM).

Test Example 5
(Solubility Test 5)

The solubility test 1 was repeated except that the modified t-PA was replaced with natural t-PA prepared in Preparation Example 2 and that a buffer solution containing 40 mM of citric acid was used. In the test, the change in the solubility of natural t-PA with varied concentration of nicotinamide to be combined with the buffer solution was determined. The results are shown in Table 5. The basic buffer solution used in the test had the following composition:

Composition of basic buffer solution: 40 mM citrate buffer/0.01% Tween 80 (pH 7.2).

The buffer solution will be referred to as "buffer A".

TABLE 5

| Sample No. | Composition of buffer | Solubility of natural t-PA ($\mu$g/ml) | Solubility of modified t-PA ($\mu$g/ml) |
|---|---|---|---|
| 8 | buffer A | 1270 | 247 |
| 9 | buffer A + 0.1% NA | 1425 | — |
| 10 | buffer A + 0.3% NA | 1467 | 424 |
| 11 | buffer A + 1.0% NA | 2410 | 1065 |
| 12 | buffer A + 3.0% NA | 6121 | 4392 |
| 13 | buffer A + 4.0% NA | 8225 | 6871 |
| 14 | buffer A + 5.0% NA | >9308 | 7370 |

Note) NA represents nicotinamide.

It is understood from the results shown in Table 5 that the solubility of also the natural t-PA is improved by the addition of nicotinamide. It is also understood that the solubility of natural t-PA is generally higher than that of modified t-PA.

Test Example 6
(Freeze-drying Test 1)

On the basis of the results obtained in Solubility Test Examples 1 to 5, a freeze-dried preparation of modified t-PA was prepared from the following formulation.

The modified t-PA precipitate stored in frozen state was dissolved in a buffer solution having a twice concentration to adjust the t-PA concentration to 3 mg/ml. After the filtration and sterilization, the obtained liquid was fed into glass vials and then freeze-dried by the following steps:

(1) After freezing at a shelf temperature of −50° C. for 2 hours and then −24° C. for 1 hour, the frozen product was subjected to the preliminary freezing at −50° C. for 15 hours.

(2) The shelf temperature was elevated to −5° C. under reduced pressure of 0.1 Torr to conduct the primary drying.

(3) After the completion of the primary drying, the shelf temperature was elevated to 30° C. to conduct the secondary drying.

Formulation

| citrate buffer solution | 100 mM |
|---|---|
| nicotinamide | 1.25% |
| mannitol | 1% |
| Tween 80 | 0.01% |
| modified t-PA | 1.5 mg/ml |
| (pH 5.6) | |

The freeze-dried preparation thus obtained was dissolved in water-for-injection. In this step, the freeze-dried preparation was immediately dissolved in water to form a transparent solution. In the obtained injection, the activity of the modified t-PA and the normal protein structure were kept. It is apparent from the results of Test Example 6 that the freeze-dried preparation of modified t-PA of a high concentration can be produced.

The same test as that described above was repeated except that 40 mM citrate buffer solution was used. The effects similar to those obtained as described above were obtained.

Test Example 7
(Stability Test 1 of Freeze-dried Sample)

The freeze-dried sample obtained in Test Example 6 was left to stand at 60° C. for a predetermined period of time to examine its stability. The stability was evaluated on the basis of the deterioration in the hydrolysis activity on a synthetic substrate (S-2288) and the main peak persistence in anion exchange (DEAE) HPLC analysis.

The hydrolysis activity on the synthetic substrate was determned according to Pharmacopeial Previews, p. 1223, November–December (1990). In the analysis according to the anion exchange HPLC, an anion exchange column (DEAE-5PW; a product of Tosoh Corporation) and 10 mM tris hydrochloride buffer solution (pH 8.0) as the mobile phase were used. The gradient elution was conducted with an eluent containing 0.2 M of sodium chloride.

The results are shown in the following Table 6.

TABLE 6

| Time of leaving to stand (hrs.) | Activity persistence (%) | Main peak persistence (%) | Appearance of solution |
|---|---|---|---|
| 0 | 100.0 | 100.0 | colorless, transparent solution |
| 86 | 101.4 | 94.3 | colorless, transparent solution |
| 163 | 106.5 | 95.3 | colorless, transparent solution |

It will be understood from the results shown in Table 6 that nicotinamide is effective not only in solubilizing t-PA but also in stabilizing the freeze-dried state. It is thus possible to produce a highly stable preparation by using the nicotinamide-containing medicinal preparation.

Test Example 8
(Stability Test 1 of Liquid Preparation)

The modified t-PA was dissolved in the nicotinamide-containing buffer and the resultant solution was left to stand at 40° C. to examine the stability.

The stability was evaluated in the same manner as that of Test Example 7. The results are shown in the following Table 7.

TABLE 7

| Time of leaving to stand (hrs.) | Activity persistence (%) | Main peak persistence (%) | Appearance of solution |
|---|---|---|---|
| 0 | 100.0 | 100.0 | colorless, transparent solution |
| 86 | 88.0 | 101.3 | colorless, transparent solution |
| 171 | 87.5 | 88.0 | colorless, transparent solution |

It will be understood from the results shown in Table 7 that the properties of the nicotinamide-containing medicinal composition can be kept stable also when the composition is in liquid form. It was confirmed particularly in the anion exchange HPLC analysis that the increase of the modified product by heating is inhibited and the main peak is kept.

This effect was obtained also when the citrate buffer solution was used.

In the present invention, the solubility and stability of t-PA are improved by using t-PA in combination with nicotinamide or a derivative thereof. Therefore, the present invention is effective in providing a clinically usable t-PA preparation such as a freeze dried t-PA preparation.

What is claimed is:

1. A tissue plasminogen activator medicinal composition, comprising (a) a tissue plasminogen activator in an amount of 0.005 to 1% by wt. based on the medicinal composition, and (b) a nicotinamide or a compound thereof in an amount of 0.3 to 50 w/v % based on the medicinal composition.

2. The tissue plasminogen activator medicinal composition of claim 1, further comprising citric acid.

3. The tissue plasminogen activator medicinal composition of claim 1, being in the form of a freeze-dried preparation.

4. The tissue plasminogen activator medicinal composition of claim 1, wherein said tissue plasminogen activator is a modified tissue plasminogen activator.

5. The tissue plasminogen activator medicinal composition of claim 4, wherein said modified tissue plasminogen activator is selected from the group consisting of:

(1) modified t-PA obtained by replacing Val at the 245-position of the t-PA with Met;
   (2) modified t-PA obtained by replacing Cys at the 84-position of the t-PA with Ser;
   (3) modified t-PA obtained by partially deleting the F and G domains of t-PA and replacing Asn at the 117-position with Glu;
   (4) modified t-PA obtained by deleting the K1 domain of t-PA and replacing Arg at the 275-position with Glu; and
   (5) modified t-PA obtained by deleting the F, G and K1 domains of t-PA.

6. The tissue plasminogen activator medicinal composition of claim 1, comprising 0.01 to 0.5% by wt of said tissue plasminogen activator (a).

7. The tissue plasminogen activator medicinal composition of claim 1, comprising 0.1 to 0.2% by wt of said tissue plasminogen activator (a).

8. The tissue plasminogen activator medicinal composition of claim 1, comprising 1 to 3% w/v % of said nicotinamide(b) or compound thereof.

9. A process for preparing a medicinal composition containing a tissue plasminogen activator in an amount of 0.005 to 1% by wt., and a nicotinamide or a compound thereof in an amount of 0.3 to 50 w/v %, based on the medicinal composition, which process comprises dissolving said tissue plasminogen activator in a medium containing said nicotinamide or a said compound thereof.

10. The process of claim 9, wherein citric acid is further contained in said medium in a concentration of 10 to 500 mM.

11. The process of claim 9, wherein said tissue plasminogen activator is a modified tissue plasminogen activator.

12. The process of claim 10, wherein said modified tissue plasminogen activator is selected from the group consisting of:

(1) modified t-PA obtained by replacing Val at the 245-position of the t-PA with Met;
   (2) modified t-PA obtained by replacing Cys at the 84-position of the t-PA with Ser;
   (3) modified t-PA obtained by partially deleting the F and G domains of t-PA and replacing Asn at the 117-position with Glu;
   (4) modified t-PA obtained by deleting the K1 domain of t-PA and replacing Arg at the 275-position with Glu; and
   (5) modified t-PA obtained by deleting the F, G and K1 domains of t-PA.

13. The process of claim 9, wherein said tissue plasminogen activator medicinal composition comprises 0.01 to 0.5% by wt of said tissue plasminogen activator.

14. The process of claim 13, wherein said amount is 0.1 to 0.2% by wt.

15. The process of claim 9, wherein said tissue plasminogen activator medicinal composition comprises 1 to 3 w/v % of said nicotinamide or compound thereof.

16. The process of claim 9, wherein said compound of nicotinamide is an N-alkyl-substituted nicotinamide, wherein said alkyl has 1 to 5 carbon atoms.

17. The process of claim 16, wherein said compound of claim 16, wherein said compound of nicotinamide is N-methylnicotinamide or N,N-dimethyl-nicotinamide.

* * * * *